United States Patent
Pack et al.

(10) Patent No.: US 7,728,027 B2
(45) Date of Patent: Jun. 1, 2010

(54) PROCESS FOR SYNTHESIZING COMPOUNDS USEFUL FOR TREATING HEPATITIS C

(75) Inventors: Shawn K. Pack, Plainsboro, NJ (US); Peng Geng, Edison, NJ (US); Michael J. Smith, Somerset, NJ (US); Jason Hamm, Clark, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 16 days.

(21) Appl. No.: 12/174,860

(22) Filed: Jul. 17, 2008

(65) Prior Publication Data

US 2009/0043107 A1    Feb. 12, 2009

Related U.S. Application Data

(60) Provisional application No. 60/954,595, filed on Aug. 8, 2007.

(51) Int. Cl.
| | |
|---|---|
| *A61K 31/445* | (2006.01) |
| *A61K 31/422* | (2006.01) |
| *A61K 31/427* | (2006.01) |
| *A61K 31/4178* | (2006.01) |
| *A61K 31/5377* | (2006.01) |
| *A61K 31/541* | (2006.01) |
| *C07D 233/64* | (2006.01) |
| *C07D 211/06* | (2006.01) |
| *C07D 263/04* | (2006.01) |
| *C07D 265/30* | (2006.01) |
| *C07D 277/04* | (2006.01) |
| *C07D 279/10* | (2006.01) |

(52) U.S. Cl. .......... 514/397; 514/227.8; 514/231.5; 514/317; 544/56; 544/106; 546/208; 548/146; 548/215; 548/311.1

(58) Field of Classification Search .......... 548/311.1, 548/145, 215; 514/397, 227.8, 231.5, 317; 544/56, 106; 546/208
See application file for complete search history.

(56) References Cited

U.S. PATENT DOCUMENTS 5,654,451 A    8/1997    Kari

FOREIGN PATENT DOCUMENTS

| WO | WO 94/15909 | 7/1994 |
|---|---|---|
| WO | WO 2006/093867 | 9/2006 |
| WO | WO 2006/133326 | 12/2006 |
| WO | WO 2007/031791 | 3/2007 |
| WO | WO-2007/031791 A2 * | 3/2007 |
| WO | WO 2007/058384 | 5/2007 |
| WO | WO 2007/077186 | 7/2007 |
| WO | WO 2007/138242 | 12/2007 |
| WO | WO 2008/021927 | 2/2008 |
| WO | WO 2008/021928 | 2/2008 |
| WO | WO 2008/021936 | 2/2008 |
| WO | WO 2008/133753 | 11/2008 |

OTHER PUBLICATIONS

U.S. Appl. No. 12/029,680, filed Feb. 12, 2008, Bachand et al.
U.S. Appl. No. 12/030,232, filed Feb. 13, 2008, Bachand et al.
U.S. Appl. No. 12/120,494, filed May 14, 2008, Bachand et al.
U.S. Appl. No. 12/175,104, filed Jul. 17, 2008, Kim et al.

* cited by examiner

*Primary Examiner*—Kamal A Saeed
*Assistant Examiner*—Janet L Coppins
(74) *Attorney, Agent, or Firm*—Pamela A. Mingo

(57) ABSTRACT

The present disclosure generally relates to a process for synthesizing methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate dihydrochloride salt. The present disclosure also generally relates to intermediates useful in this process.

22 Claims, No Drawings

PROCESS FOR SYNTHESIZING COMPOUNDS USEFUL FOR TREATING HEPATITIS C

CROSS-REFERENCE TO RELATED APPLICATIONS

This application claims the benefit of U.S. Provisional Application Ser. No. 60/954,595 filed Aug. 8, 2007.

The present disclosure generally relates to a process for synthesizing methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate dihydrochloride salt. The present disclosure also generally relates to intermediates useful in this process.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40 percent of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

The compound methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate dihydrochloride is useful for the treatment of HCV infection.

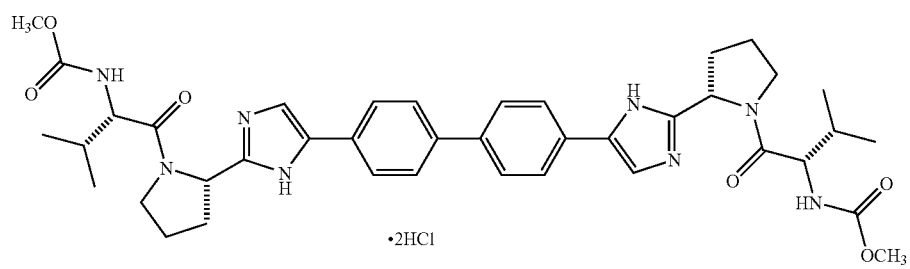

For purposes of large-scale production there is a need for a high-yielding synthesis of Compound (I) and related analogs that is both efficient and cost-effective.

In a first aspect the present disclosure provides a process for preparing a compound of formula (7)

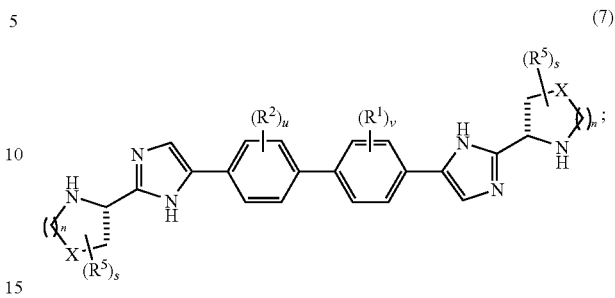

or a pharmaceutically acceptable salt thereof;

wherein
n is 0, 1, or 2;
s is 0, 1, 2, 3, or 4;
u and v are each independently selected from 0, 1, 2, or 3;
X is selected from O, S, S(O), $SO_2$, $CH_2$, $CHR^5$, and $C(R^5)_2$; provided that when n is 0, X is selected from $CH_2$, $CHR^5$, and $C(R^5)_2$;
$R^1$ and $R^2$ are each independently selected from alkoxy, alkyl, and halo; and
when s is 2, 3, or 4, each $R^5$ on the ring is independently selected from alkoxy, alkyl, and aryl, wherein the alkyl can optionally form a fused three- to six-membered ring with an adjacent carbon atom, wherein the three- to six-membered ring is optionally substituted with one or two alkyl groups;

provided that the two heterocyclic rings substituting the imidazole rings are identical; the process comprising:
(a) reacting a compound of formula (3)

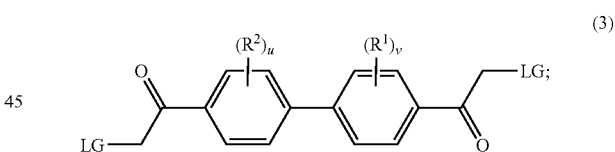

wherein
u, v, $R^1$, and $R^2$ are as described for formula (7); and
LG is a leaving group;

with a compound of formula (4)

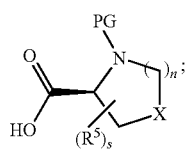
(4)

wherein PG is a nitrogen protecting group;
(b) treating the product of step (a) with a reagent selected from ammonium acetate, ammonium formate, ammonium sulfamate, ammonium phosphate, ammonium citrate, ammonium carbamate, and ammonia; and
(c) treating the product of step (b) with a deprotecting agent.

In a first embodiment of the first aspect n is 1; s is 0; u and v are each 0; and X is $CH_2$.

In a second embodiment of the first aspect LG is a halide. In a third embodiment of the first aspect the halide is a bromide.

In a fourth embodiment of the first aspect step (a) is conducted with a base. In a fifth embodiment of the first aspect the base is diisopropylethylamine.

In a sixth embodiment of the first aspect the reagent used in step (b) is ammonium acetate.

In seventh embodiment of the first aspect PG is represented by the formula:

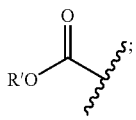

wherein $\mathcal{S}$ denotes the point of attachment to the parent molecular moiety; and R' is selected from alkyl, aryl, and arylalkyl. In an eighth embodiment of the first aspect PG is tert-butoxycarbonyl.

In a ninth embodiment of the first aspect the deprotecting agent of step (c) is an acid. In a tenth embodiment of the first aspect the acid is hydrochloric acid.

In a second aspect the present disclosure provides a process for preparing a compound of formula (I)

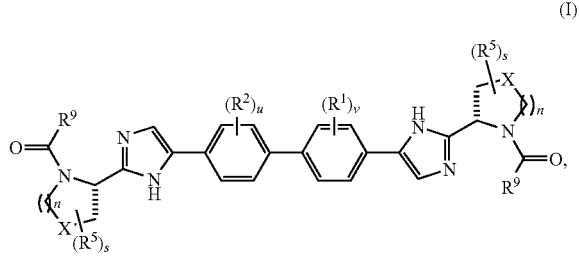
(I)

wherein
n is 0, 1, or 2;
s is 0, 1, 2, 3, or 4;
u and v are each independently selected from 0, 1, 2, or 3;
X is selected from O, S, S(O), $SO_2$, $CH_2$, $CHR^5$, and $C(R^5)_2$; provided that when n is 0, X is selected from $CH_2$, $CHR^5$, and $C(R^5)_2$;
$R^1$ and $R^2$ are each independently selected from alkoxy, alkyl, and halo; and when s is 2, 3, or 4, each $R^5$ on the ring is independently selected from alkoxy, alkyl, and aryl, wherein the alkyl can optionally form a fused three- to six-membered ring with an adjacent carbon atom, wherein the three- to six-membered ring is optionally substituted with one or two alkyl groups;

provided that the two heterocyclic rings substituting the imidazole rings are identical; and $R^9$ is selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, $-NR^cR^d$, $(NR^cR^d)$alkenyl, $(NR^cR^d)$alkyl, and $(NR^cR^d)$carbonyl;

the process comprising:

(a) reacting a compound of formula (3)

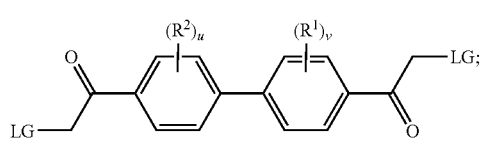
(3)

wherein
u, v, $R^1$, and $R^2$ are as described for formula (7); and
LG is a leaving group;

with a compound of formula (4)

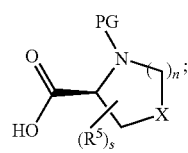
(4)

wherein PG is a nitrogen protecting group;

(b) treating the product of step (a) with a reagent selected from ammonium acetate, ammonium formate, ammonium sulfamate, ammonium phosphate, ammonium citrate, ammonium carbamate, and ammonia; and (c) treating the product of step (b) with a deprotecting agent to provide a compound of formula (7)

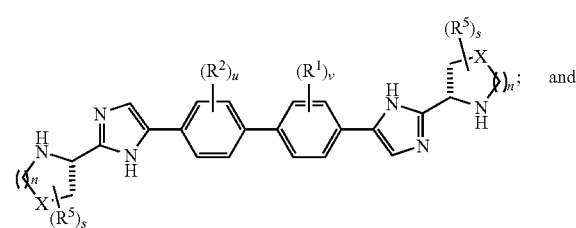
(7)

and (d) treating the compound of formula (7) with a compound of formula (8)

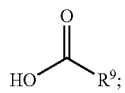

wherein $R^9$ is as defined above.

In a first embodiment of the second aspect n is 1; s is 0; u and v are each 0; and X is $CH_2$.

In a second embodiment of the second aspect LG is a halide. In a third embodiment of the second aspect the halide is a bromide.

In a fourth embodiment of the second aspect step (a) is conducted with a base. In a fifth embodiment of the second aspect the base is diisopropylethylamine.

In a sixth embodiment of the second aspect the reagent used in step (b) is ammonium acetate.

In a seventh embodiment of the second aspect PG is represented by the formula:

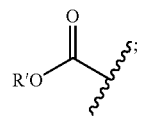

wherein

⌇ denotes the point of attachment to the parent molecular moiety; and

R' is selected from alkyl, aryl, and arylalkyl. In a fifth embodiment of the second aspect PG is tert-butoxycarbonyl.

In an eighth embodiment of the second aspect the deprotecting agent of step (c) is an acid. In a ninth embodiment of the second aspect the acid is hydrochloric acid.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

As used in the present specification, the following terms have the meanings indicated:

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms. In the compounds of the present disclosure, when m and/or n is 1 or 2; X and/or Y is $CHR^5$ and/or $CHR^6$, respectively, and $R^5$ and/or $R^6$ is alkyl, each alkyl can optionally form a fused three- to six-membered ring with an adjacent carbon atom to provide one of the structures shown below:

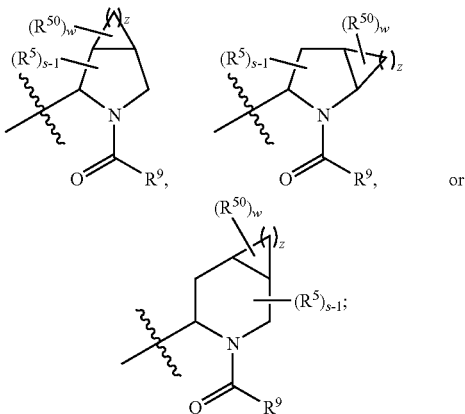

where z is 1, 2, 3, or 4, w is 0, 1, or 2, and $R^{50}$ is alkyl. When w is 2, the two $R^{50}$ alkyl groups may be the same or different.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^x$R$^y$, (NR$^x$R$^y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The term "base," as used herein, refers to a reagent capable of accepting protons during the course of a reaction without acting as a nucleophile. Examples of bases include disilylamides such as lithium hexamethyldisilazide, non-nucleophilic amines such as triethylamine, diisopropylethylamine, and diisopropylamine; heterocyclic amines such as imidazole, pyridine, pyridazine, and pyrimidine; and bicyclic amines such as DBN (1,5-diazabicyclo[4.3.0]non-5-ene) and DBU (1,8-diazabicyclo[5.4.0]undec-7-ene. The base chosen for a particular conversion depends on the nature of the starting materials, the solvent or solvents in which the reaction is conducted, and the temperature at which the reaction is conducted.

The term "carbonyl," as used herein, refers to —C(O)—.

The term "carboxy," as used herein, refers to —CO$_2$H.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —NR$^c$R$^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "deprotecting agent," as used herein, refers to a substance capable of removing a nitrogen protecting group. Examples of deprotecting agents include acids such as trifluoroacetic acid and hydrochloric acid; silyl agents such as trimethylsilyl iodide; and cyclic amines such as morpholine. Additional examples of deprotecting agents, as well as the protecting groups these agents can remove, can be found in Greene, T. W. and Wuts, P. G. M., "Protective Groups in Organic Synthesis", 3$^{rd}$ edition.

The term "formyl," as used herein, refers to —CHO.

The terms "halo" and "halide," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "leaving group," as used herein, refers to a group that is capable of being displaced by a nucleophile in an SN2 reaction. Representative leaving groups include sulfonates such as tosylate, mesylate, and benzylsulfonate; and halides such as bromo, chloro, and iodo.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (NR$^e$R$^f$)alkyl, NR$^e$R$^f$) alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to an alkenyl group substituted with one, two, or three —NR$^c$R$^d$ groups.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "(NR$^c$R$^d$)carbonyl," as used herein, refers to an —NR$^c$R$^d$ group attached to the parent molecular moiety through a carbonyl group.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR^xR^y)carbonyl," as used herein, refers to an —NR^xR^y group attached to the parent molecular moiety through a carbonyl group.

The term "oxo," as used herein, refers to =O.

All of the processes in the present disclosure can be conducted as continuous processes. The term "continuous process," as used herein, represents steps conducted without isolation of the intermediate.

Scheme 1

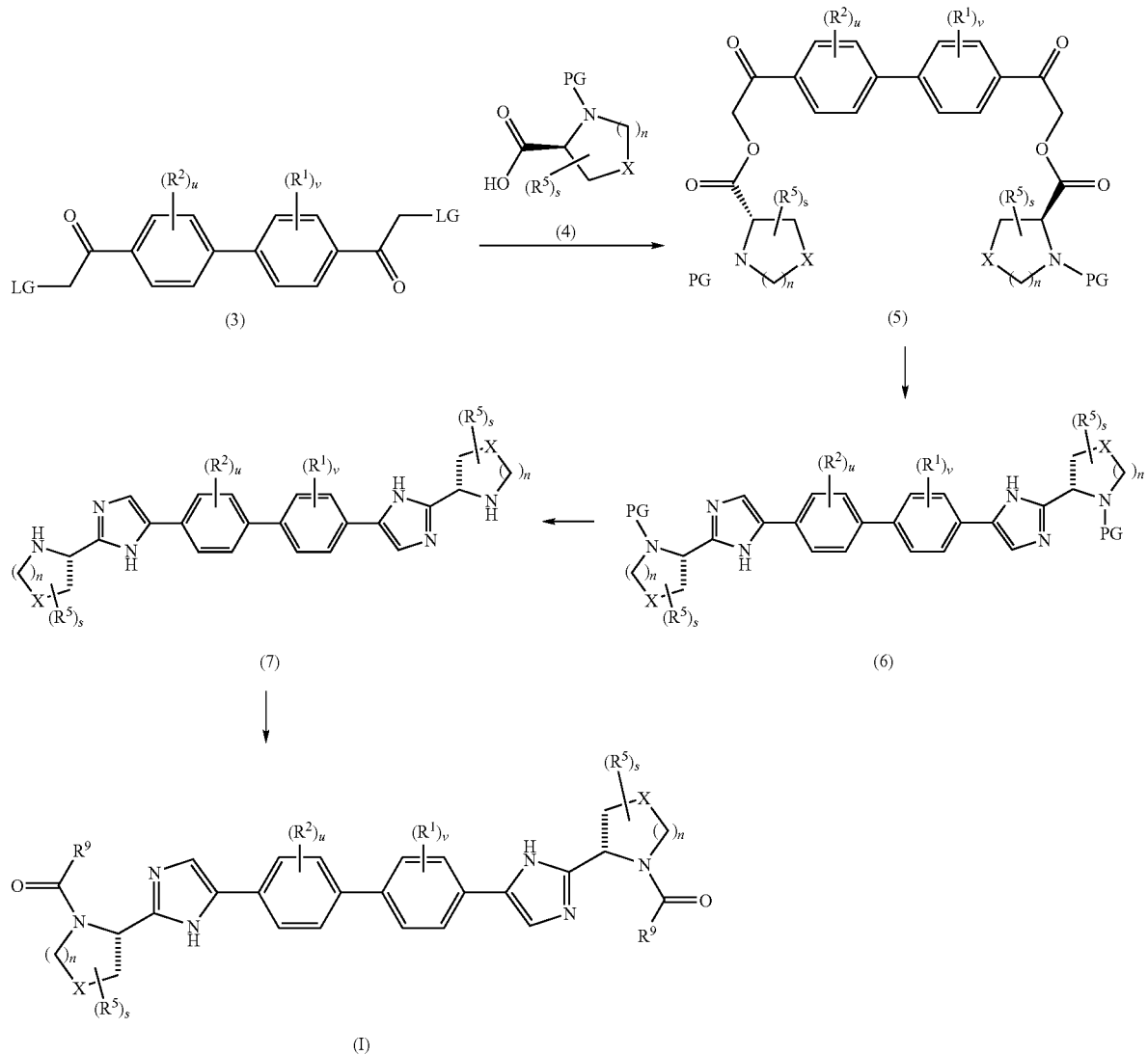

The term "nitrogen protecting group," as used herein, represents groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, and the like.

The term "sulfonyl," as used herein, refers to —SO$_2$—.

Scheme 1 illustrates the synthesis of compounds of formula (I). Compounds of formula (3), which can be synthesized using the method described in the Examples, can be reacted with compounds of formula (4) (which are commercially available or synthesized by methods known to those of ordinary skill in the art) in the presence of a non-nucleophilic base to provide compounds of formula (5). Examples of non-nucleophilic bases include diisopropylethylamine, triethylamine, hexamethyldisilane, and diisopropylamine. Examples of solvents used in this reaction include acetonitrile, tetrahydrofuran, ethyl acetate, isopropyl acetate, butyl acetate, toluene, tetrahydropyran, acetone, DMSO, DMF, DMA, NMP, and dichloromethane. The reaction is typically conducted at a temperature of about 20° C. to about 40° C. and reaction times are typically about 1 to about 12 hours.

Compounds of formula (5) can be converted to compounds of formula (6) by treatment with ammonium acetate, ammonium formate, ammonium sulfamate, ammonium phosphate, ammonium citrate, ammonium carbamate, or ammonia. Examples of solvents used in this reaction include toluene, xylene, mesitylene, and acetic acid. The reaction is typically conducted at a temperature of about 85° C. to about 110° C. and reaction times are typically about 10 to about 20 hours.

Compounds of formula (7) can be prepared by deprotection of the protecting group contained in the compounds of formula (6). Representative deprotecting agents include HCl (for tert-butoxycarbonyl protecting groups), trimethylsilyl iodide (for methoxy- and ethoxycarbonyl protecting groups), and morpholine (for 9-fluorenylmethoxycarbonyl protecting groups). Reaction conditions and times vary with the choice of deprotecting agent and will be known to those of ordinary skill in the art.

Compounds of formula (7) can be converted to compounds of formula (I) by coupling with an appropriately substituted amino acid in the presence of coupling agents such as 1,1'-carbonyldiimidazole, bis(2-oxo-3-oxazolidinyl)phosphinic chloride, 1-hydroxy-7-azabenzotriazole, 1-hydroxybenzotriazole hydrate, 3-hydroxy-1,2,3-benzotriazin-4(3H)-one, 1-(3-dimethyaminopropyl)-3-ethylcarbodiimide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, Boc-L-valine anhydride, and mixtures thereof. Examples of solvents include isopropyl acetate, acetone, NMP, dichloromethane, 2-methyltetrahydrofuran, ethyl acetate, and acetonitrile. Particular conditions will vary depending on the nature of the coupling reagent and will be known to those of ordinary skill in the art.

The following non-limiting examples are illustrative of the disclosure.

EXAMPLES

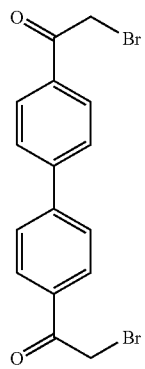

Preparation of Compound (3)

A 1 L, 3-neck round bottom flask, fitted with a nitrogen line, overhead stirrer and thermocouple, was charged with 20 g (83.9 mmol, 1 equiv) 1,1'-(biphenyl-4,4'-diyl)diethanone, 200 mL CH$_2$Cl$_2$ and 8.7 mL (27.1 g, 169.3 mmol, 2.02 quiv) bromine. The mixture was allowed to stir under nitrogen for about 20 hours under ambient conditions. The resulting slurry was charged with 200 mL CH$_2$Cl$_2$ and concentrated down to about 150 mL via vacuum distillation. The slurry was then solvent exchanged into tetrahydrofuran (THF) to a target volume of 200 mL via vacuum distillation. The slurry was cooled to 20-25° C. over 1 hour and allowed to stir at 20-25° C. for an additional hour. The off-white crystalline solids were filtered and washed with 150 mL CH$_2$Cl$_2$. The product was dried under vacuum at 60° C. to yield 27.4 g (69.2 mmol, 82%) of the desired product: $^1$H NMR (400 MHz, CDCl$_3$) δ 7.95-7.85 (m, 4H), 7.60-7.50 (m, 4H), 4.26 (s, 4H); $^{13}$C NMR (100 MHz, CDCl$_3$) δ 191.0, 145.1, 133.8, 129.9, 127.9, 30.8; IR (KBr, cm-1) 3007, 2950, 1691, 1599, 1199; Anal calcd for C$_{16}$H$_{12}$Br$_2$O$_2$: C, 48.52; H, 3.05; Br, 40.34. Found: C, 48.53; H, 3.03; Br, 40.53. HRMS calcd for C$_{16}$H$_{13}$Br$_2$O$_2$ (M+H; DCI$^+$): 394.9282. Found: 394.9292. mp 224-226° C.

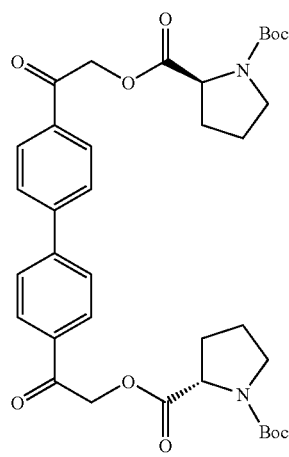

Preparation of Compound (5)

A 500 mL jacketed flask, fitted with a nitrogen line, thermocouple and overhead stirrer, was charged with 20 g (50.5 mmol, 1 equiv) of Compound 3, 22.8 g (105.9 moles, 2.10 equiv) 1-(tert-butoxycarbonyl)-L-proline and 200 mL acetonitrile. The slurry was cooled to 20° C. followed by the addition of 18.2 mL (13.5 g, 104.4 mmol, 2.07 equiv) diisopropylethylamine (DIPEA). The slurry was warmed to 25° C. and allowed to stir for 3 hours. The resulting clear, organic solution was washed with 3×100 mL 13 wt % aqueous NaCl. The rich acetonitrile solution was solvent exchanged into toluene (target volume=215 mL) by vacuum distillation until there was less than 0.5 vol % acetonitrile.

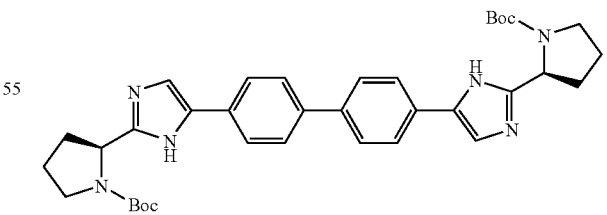

Preparation of Compound (6)

The toluene solution of Compound 5 was charged with 78 g (1.011 moles, 20 equiv) ammonium acetate and heated to 95-100° C. The mixture was allowed to stir at 95-100° C. for 15 hours. After reaction completion, the mixture was cooled to 70-80° C. and charged with 7 mL acetic acid, 40 mL n-butanol, and 80 mL of 5 vol % aqueous acetic acid. The resulting biphasic solution was split while maintaining a temperature >50° C. The rich organic phase was charged with 80 mL of 5 vol % aqueous acetic acid, 30 mL acetic acid and 20 mL n-butanol while maintaining a temperature >50° C. The resulting biphasic solution was split while maintaining a temperature >50° C. and the rich organic phase was washed with an additional 80 mL of 5 vol % aqueous acetic acid. The rich organic phase was then solvent exchanged into toluene to a target volume of 215 mL by vacuum distillation. While maintaining a temperature >60° C., 64 mL methanol was charged. The resulting slurry was heated to 70-75° C. and aged for 1 hour. The slurry was cooled to 20-25° C. over 1 hour and aged at that temperature for an additional hour. The slurry was filtered and the cake was washed with 200 mL 10:3 toluene: methanol. The product was dried under vacuum at 70° C., resulting in 19.8 g (31.7 mmol, 63%) of the desired product: $^1$H NMR (400 MHz, DMSO-$d_6$) δ 13.00-11.00 (s, 2H), 7.90-7.75 (m, 4H), 7.75-7.60 (m, 4H), 7.60-7.30 (s, 2H), 4.92-4.72 (m, 2H), 3.65-3.49 (m, 2H), 3.49-3.28 (m, 2H), 2.39-2.1 (m, 2H), 2.10-1.87 (m, 6H), 1.60-1.33 (s, 8H), 1.33-1.07 (s, 10H); $^{13}$C NMR (100 MHz, DMSO-$d_6$) δ 154.1, 153.8, 137.5, 126.6, 125.0, 78.9, 78.5, 55.6, 55.0, 47.0, 46.7, 33.7, 32.2, 28.5, 28.2, 24.2, 23.5; IR (KBr, cm-1) 2975, 2876, 1663, 1407, 1156, 1125; HRMS calcd for $C_{36}H_{45}N_6O_4$ (M+H; ESI$^+$): 625.3502. Found: 625.3502. mp 190-195° C. (decomposed).

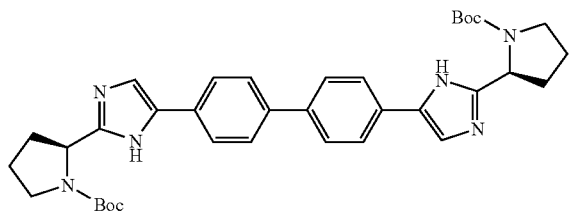

Alternative Preparation of Compound (6)

The toluene solution of Compound 5 was charged with 78 g (1.011 moles, 20 equiv) ammonium acetate and heated to 95-100° C. The mixture was allowed to stir at 95-100° C. for 15 hours. After reaction completion, the mixture was cooled to 50-60° C. and charged with 140 mL of 2:1 acetic acid: water. The resulting biphasic solution was split while maintaining a temperature >50° C. The organic layer was washed with 70 mL 1:1 acetic acid:water. The rich aqueous layers were combined and the residual toluene removed via vacuum distillation. While maintaining a temperature of 50-60° C., 50 mL methanol was charged followed by 68 mL 10 N NaOH. The resulting slurry was cooled to 20-25° C. over 1 hour and aged at that temperature for an additional hour. The slurry was filtered and the cake was washed with 200 mL water followed by 75 mL MeOH. The product was dried under vacuum at 70° C., resulting in 27.4 g of crude product. A 1 L jacketed flask, equipped with a nitrogen line, overhead stirrer and thermocouple was charged with 63 mL NMP and 25 g of the above crude product. The mixture was heated to 50-60° C. and charged with 83 mL MeOH. The resulting slurry was allowed to stir at 50-60° C. for 18 hours. The slurry was then charged with 208 mL MeOH while maintaining a temperature >50° C. The slurry was cooled to ambient temperature over 1.5 hours and stirred for an additional 2 hours. The solids were filtered, washed with 75 mL MeOH and dried under vacuum @70° C. to give 18.0 g (28.8 mmol, 62% adjusted) of the desired product.

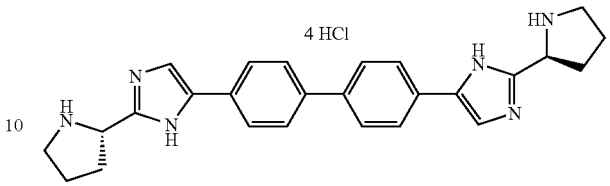

Preparation of Compound (7)

To a 250 mL reactor equipped with a nitrogen line and overhead stirrer, 25.0 g of Compound 6 (40.01 mmol, 1 equiv) was charged followed by 250 mL methanol and 32.85 mL (400.1 mmol, 10 equiv) 6M aqueous HCl. The temperature was increased to 50° C. and agitated at 50° C. for 5 hours. The resulting slurry was cooled to 20-25° C. and held with agitation for about 18 hours. Filtration of the slurry afforded a solid which was washed successively with 100 mL 90% methanol/water (V/V) and 2×100 mL of methanol. The wet cake was dried in a vacuum oven at 50° C. overnight to give 18.12 g (31.8 mmol, 79.4%) of the desired product.

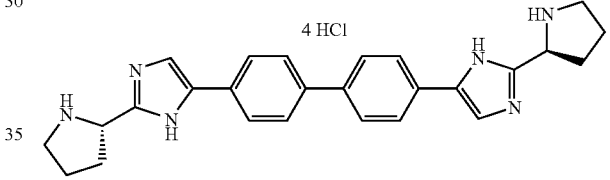

Alternative Preparation of Compound (7)

A jacketed reactor equipped with a mechanical stirrer, thermocouple and a nitrogen inlet was charged with 2.8 L isopropyl alcohol, 1.32 L water, and 1 kg of Compound 6 (1.6 moles, 1 equiv). The slurry was then charged with 1.31 L (1.58 kg, 16.0 moles, 10 equiv) concentrated hydrogen chloride at ambient temperature in 30 min. The resulting solution was heated to 50° C. and allowed to stir for 2.5 hours. The product was crystallized by the addition of 7.2 L isopropyl alcohol and the slurry was cooled to ambient temperature. The product was collected by filtration and washed with 3.7 L 20% water/isopropyl alcohol followed by 7.4 L isopropyl alcohol. The wet cake was dried in a vacuum oven at 50° C. to give 0.84 kg (1.44 moles, 90%) of the desired product.

Recrystallization of Compound (7)

To a 250 mL reactor equipped with a nitrogen line and an overhead stirrer, 17.8 g of Compound 7 from above was charged followed by 72 mL methanol. The resulting slurry was agitated at 50° C. for 4 hours, cooled to 20-25° C. and held with agitation at 20-25° C. for 1 hour. Filtration of the slurry afforded a crystalline solid which was washed with 60 mL methanol. The resulting wet cake was dried in a vacuum oven at 50° C. for 4 days to yield 14.7 g (25.7 mmol, 82.6%) of the purified product: $^1$H NMR (400 MHz, DMSO-$d_6$) δ 10.5-10.25 (br, 2H), 10.1-9.75 (br, 2H), 8.19 (s, 2H), 7.05 (d, J=8.4, 4H), 7.92 (d, J=8.5, 4H), 5.06 (m, 2H), 3.5-3.35 (m, 4H), 2.6-2.3 (m, 4H), 2.25-2.15 (m, 2H), 2.18-1.96 (m, 2H); $^{13}$C NMR (100 MHz, DMSO-d$_6$) δ 156.6, 142.5, 139.3, 128.1, 127.5, 126.1, 116.9, 53.2, 45.8, 29.8, 24.3; IR (KBr, cm$^{-1}$) 3429, 2627, 1636, 1567, 1493, 1428, 1028. Anal calcd for C$_{26}$H$_{32}$N$_6$Cl$_4$: C, 54.75; H, 5.65; Cl, 24.86; Adjusted for 1.9% water: C, 53.71; H, 5.76; N, 14.46; Cl, 24.39. Found: C, 53.74; H, 5.72; N, 14.50; Cl, 24.49; KF=1.9. mp 240° C. (decomposed).

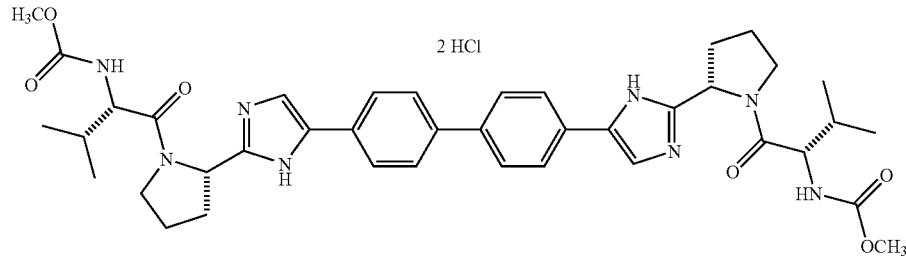

Preparation of Compound (I)

A 1 L jacketed flask equipped with a nitrogen line and an overhead stirrer was sequentially charged with 100 mL acetonitrile, 13.69 g (89.4 mmol, 2.5 equiv) hydroxybenzotriazole hydrate, 15.07 g (86 mmol, 2.4 equiv) N-(methoxycarbonyl)-L-valine, 16.46 g (85.9 mmol, 2.4 equiv) 1-(3-dimethyaminopropyl)-3-ethylcarbodiimide hydrochloride and an additional 100 mL acetonitrile. The resulting solution was agitated at 20° C. for 1 hour and charged with 20.4 g (35.8 mmol, 1 equiv) of purified Compound 7. The slurry was cooled to about 0° C. and 18.47 g (142.9 mmol, 4 equiv) diisopropylethylamine was added over 30 minutes while maintaining a temperature below 10° C. The solution was slowly heated to 15° C. over 3 hours and held at 15° C. for 12 hours. The resulting solution was charged with 120 mL 13 wt % aqueous NaCl and heated to 50° C. for 1 hour. After cooling to 20° C., 100 mL of isopropyl acetate was added. The biphasic solution was filtered through a 0.45 μm filter and the mixture split. The rich organic phase was washed with 2×240 mL of a 0.5 N NaOH solution containing 13 wt % NaCl followed by 120 mL 13 wt % aqueous NaCl. The mixture was then solvent exchanged into isopropyl acetate by vacuum distillation with a target volume of 400 mL. The resulting hazy solution was cooled to 20° C. and filtered through a 0.45 μm filter. The clear solution was then solvent exchanged into ethanol by vacuum distillation with a target volume of 140 mL. While maintaining a temperature of 50° C., 66.4 mL (82.3 mmol, 2.3 equiv) of 1.24M HCl in ethanol was added. The mixture was then charged with 33 mg (0.04 mmol, 0.001 equiv) of seed crystals of Compound (I) (see preparation below) and the resulting slurry was stirred at 50° C. for 3 hours. The mixture was cooled to 20° C. over 1 hour and aged at that temperature for an additional 22 hours. The slurry was filtered and the wet cake was washed with 100 mL of 2:1 acetone:ethanol. The solids were dried in a vacuum oven at 70° C. to give 22.15 g (27.3 mmol, 76.3%) of the desired product.

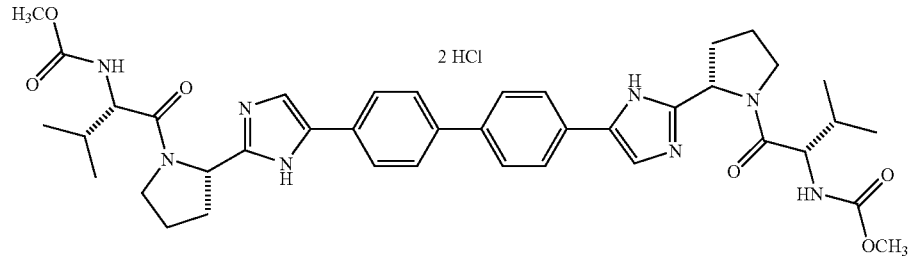

Alternative Preparation of Compound (I)

A jacketed reactor equipped with a mechanical agitator, a thermocouple and a nitrogen inlet was sequentially charged with 10 L acetonitrile, 0.671 kg (4.38 moles, 2.50 equiv) 1-hydroxybenzotriazole, 0.737 kg (4.21 moles, 2.40 equiv) N-(methoxycarbonyl)-L-valine and 0.790 kg (4.12 moles, 2.35 equiv) 1-(3-dimethyaminopropyl)-3-ethylcarbodiimide hydrochloride. The mixture was agitated at 20° C. for 1 hour, cooled to 5° C. and charged with 1 kg (1.75 moles, 1.00 equiv) Compound 7. While maintaining a temperature <10° C., 0.906 kg (7.01 moles, 4 equiv) diisopropylethylamine was added. The mixture was heated to 15-20° C. over 2 hours and agitated for an additional 15 hours. After the reaction was complete, the mixture was washed once with 6.0 L 13 wt % aqueous NaCl, twice with 6.1 L (6.12 moles, 3.5 equiv) 1.0 M aqueous NaOH containing 13 wt % NaCl and once with 6.0 L 13 wt % aqueous NaCl. Water was then removed from the rich organic solution via azeotropic distillation. The mixture was cooled to 20° C., agitated for 1 hour and filtered. The rich organic solution was then solvent exchanged into EtOH via vacuum distillation to a target volume of 5 L. While maintaining a temperature of 50° C., 3.2 L (4.0 moles, 2.3 equiv)

1.25M HCl in EtOH was charged. The mixture was seeded with 1.6 g Compound (I) (see preparation below) and agitated at 50° C. for 3 hours. The resulting slurry was cooled to 20° C. and agitated for at least 3 hours. The product was collected by filtration and washed with 5 L 2:1 acetone:EtOH to give 1.29 kg (ca. 90 wt % product) of wet crude product. A reactor equipped with an overhead agitator, nitrogen inlet and thermocouple was charged with 1.11 kg of the above crude product and 7 L methanol. The resulting solution was treated with Cuno Zeta Carbon™ 55SP. The carbon was washed with 15 L MeOH and the combined filtrate and wash was concentrated down to 4 L via vacuum distillation. The concentrated solution was charged with 5 L acetone and seeded with 1.6 g Compound (I) (see preparation below) while maintaining a temperature of 50° C. An additional 10 L acetone was charged and the resulting slurry was stirred at 50° C. for 3 hours. The slurry was cooled to 20° C. and allowed to agitate at 20° C. for 3 hours. The product was collected by filtration, washed with 5 L 2:1 acetone:EtOH and dried under vacuum at 50-60° C. to give 0.900 kg (1.11 moles, 74% adjusted) of Compound (I).

calibrated with a NIST other suitable standard are as follows: 10.3, 12.4, 12.8, 13.3, 13.6, 15.5, 20.3, 21.2, 22.4, 22.7, 23.7.

Preparation of Seed Crystals of Compound (I)

A 250 mL round-bottom flask was charged with 6.0 g (10.5 mmol, 1 equiv) Compound 5, 3.87 g (22.1 mmol, 2.1 equiv) N-(methoxycarbonyl)-L-valine, 4.45 g (23.2 mmol, 2.2 equiv) 1-(3-dimethyaminopropyl)-3-ethylcarbodiimide hydrochloride, 0.289 g (2.14 mmol, 0.2 equiv) 1-hydroxybenzotriazole, and 30 mL acetonitrile. The resulting slurry was then charged with 7.33 mL (42.03 mmol, 4 equiv) diisopropylethylamine and allowed to stir at 24-30° C. for about 18 hours. The mixture was charged with 6 mL of water and heated to 50° C. for about 5 hours. The mixture was cooled and charged with 32 mL ethyl acetate and 30 mL water. The layers were separated and the rich organic layer was washed with 30 mL of 10 wt % aqueous NaHCO$_3$, 30 mL water, and 20 mL of 10 wt % aqueous NaCl. The rich organic layer was then dried over MgSO$_4$, filtered, and concentrated down to a

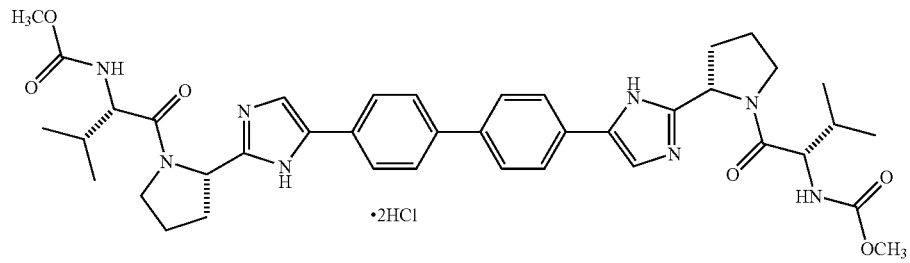

Carbon Treatment and Recrystallization of Compound (I)

A solution of Compound (I) was prepared by dissolving 3.17 g of Compound (I) from above in 22 mL methanol. The solution was passed through a 47 mm Cuno Zeta Carbon® 53SP filter at ~5 psig at a flow rate of ~58 mL/min. The carbon filter was rinsed with 32 mL of methanol. The solution was concentrated down to 16 mL by vacuum distillation. While maintaining a temperature of 40-50° C., 15.9 mL acetone and 5 mg of seed crystals of Compound (I) (see procedure below) were added. The resulting slurry was then charged with 32 mL acetone over 30 minutes. The slurry was held at 50° C. for 2 hours, cooled to 20° C. over about 1 hour and held at 20° C. for about 20 hours. The solids were filtered, washed with 16 mL 2:1 acetone:methanol and dried in a vacuum oven at 60° C. to give 2.14 g (67.5%) of purified Compound (I): $^1$H NMR (400 MHz, DMSO-d$_6$, 80° C.): 8.02 (d, J=8.34 Hz, 4H), 7.97 (s, 2H), 7.86 (d, J=8.34 Hz, 4H), 6.75 (s, 2H), 5.27 (t, J=6.44 Hz, 2H), 4.17 (t, J=6.95 Hz, 2H), 3.97-4.11 (m, 2H), 3.74-3.90 (m, 2H), 3.57 (s, 6H), 2.32-2.46 (m, 2H), 2.09-2.31 (m, 6H), 1.91-2.07 (m, 2H), 0.88 (d, J=6.57 Hz, 6H), 0.79 (d, J=6.32 Hz, 6H); $^{13}$C NMR (75 MHz, DMSO-d$_6$): δ 170.9, 156.9, 149.3, 139.1, 131.7, 127.1, 126.5, 125.9, 115.0, 57.9, 52.8, 51.5, 47.2, 31.1, 28.9, 24.9, 19.6, 17.7; IR (neat, cm$^{-1}$): 3385, 2971, 2873, 2669, 1731, 1650. Anal. Calcd for C$_{40}$H$_{52}$N$_8$O$_6$Cl$_2$: C, 59.18; H, 6.45; N, 13.80; Cl, 8.73. Found C, 59.98; H, 6.80; N, 13.68; Cl, 8.77. mp 267° C. (decomposed). Characteristic diffraction peak positions (degrees 2θ±0.1) @ RT, based on a high quality pattern collected with a diffractometer (CuKα) with a spinning capillary with 2θ residue. The crude material was then purified via flash chromatography (silica gel, 0-10% methanol in dichloromethane) to provide the free base of Compound (I).

The free-base of Compound (I) (0.03 g) was dissolved in 1 mL isopropanol at 20° C. Anhydrous HCl (70 µL, dissolved in ethanol, approximately 1.25M concentration) was added and the reaction mixture was stirred. To the solution was added methyl tert-butyl ether (1 mL) and the resulting slurry was stirred vigorously at 40° C. to 50° C. for 12 hours. The crystal slurry was cooled to 20° C. and filtered. The wet cake was air-dried at 20° C. A white crystalline solid (Form N-2 of Compound (I)) was obtained.

What is claimed is:

1. A process for preparing a compound of formula (7)

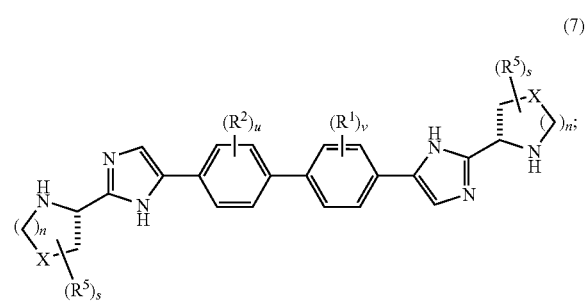

or a pharmaceutically acceptable salt thereof
wherein
n is 0, 1, or 2;
s is 0, 1, 2, 3, or 4;

u and v are each independently selected from 0, 1, 2, or 3;

X is selected from O, S, S(O), SO$_2$, CH$_2$, CHR$^5$, and C(R$^5$)$_2$;

provided that when n is 0, X is selected from CH$_2$, CHR$^5$, and C(R$^5$)$_2$;

R$^1$ and R$^2$ are each independently selected from alkoxy, alkyl, and halo;

when s is 1, 2, 3, or 4, each R$^5$ on the ring is independently selected from alkoxy, alkyl, and aryl, wherein the alkyl can optionally form a fused three- to six-membered ring with an adjacent carbon atom, wherein the three- to six-membered ring is optionally substituted with one or two alkyl groups;

provided that the two heterocyclic rings substituting the imidazole rings are identical;

the process comprising:

(a) reacting a compound of formula (3)

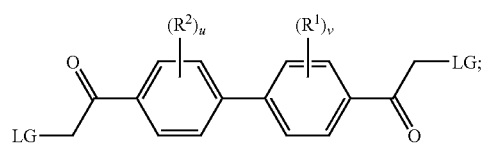

wherein u, v, R$^1$, and R$^2$ are as described for formula (7); and

LG is a leaving group;

with a compound of formula (4)

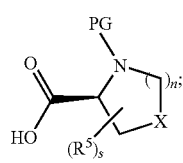

wherein PG is a nitrogen protecting group;

(b) treating the product of step (a) with a reagent selected from ammonium acetate, ammonium formate, ammonium sulfamate, ammonium phosphate, ammonium citrate, ammonium carbamate, and ammonia; and (c) treating the product of step (b) with a deprotecting agent.

2. The process of claim 1 wherein
n is 1;
s is 0;
u and v are each 0; and
X is CH$_2$.

3. The process of claim 1 wherein LG is a halide.

4. The process of claim 3 wherein the halide is a bromide.

5. The process of claim 1 wherein step (a) is conducted with a base.

6. The process of claim 5 wherein the base is diisopropylethylamine.

7. The process of claim 1 wherein the reagent used in step (b) is ammonium acetate.

8. The process of claim 1 wherein PG is represented by the formula:

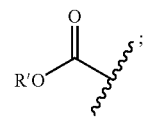

wherein

⌇ denotes the point of attachment to the parent molecular moiety; and

R' is selected from alkyl, aryl, and arylalkyl.

9. The process of claim 8 wherein PG is tert-butoxycarbonyl.

10. The process of claim 9 wherein the deprotecting agent of step (c) is an acid.

11. The process of claim 10 wherein the acid is hydrochloric acid.

12. A process for preparing a compound of formula (I)

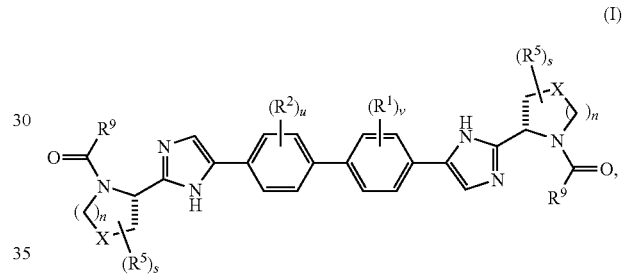

wherein n is 0, 1, or 2;

s is 0, 1, 2, 3, or 4;

u and v are each independently selected from 0, 1, 2, or 3;

X is selected from O, S, S(O), SO$_2$, CH$_2$, CHR$^5$, and C(R$^5$)$_2$;

provided that when n is 0, X is selected from CH$_2$, CHR$^5$, and C(R$^5$)$_2$;

R$^1$ and R$^2$ are each independently selected from alkoxy, alkyl, and halo;

when s is 1, 2, 3, or 4, each R$^5$ on the ring is independently selected from alkoxy, alkyl, and aryl, wherein the alkyl can optionally form a fused three- to six-membered ring with an adjacent carbon atom, wherein the three- to six-membered ring is optionally substituted with one or two alkyl groups;

provided that the two heterocyclic rings substituting the imidazole rings are identical; and R$^9$ is selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl;

the process comprising:
(a) reacting a compound of formula (3)

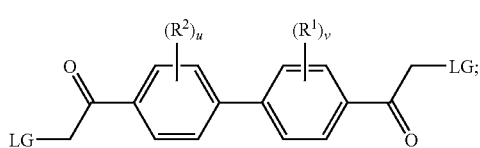

wherein
  u, v, $R^1$, and $R^2$ are as described for formula (7); and
  LG is a leaving group;
with a compound of formula (4)

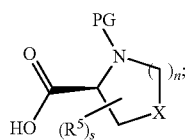

wherein PG is a nitrogen protecting group;
(b) treating the product of step (a) with a reagent selected from ammonium acetate, ammonium formate, ammonium sulfamate, ammonium phosphate, ammonium citrate, ammonium carbamate, and ammonia; and;
(c) treating the product of step (b) with a deprotecting agent to provide a compound of formula (7)

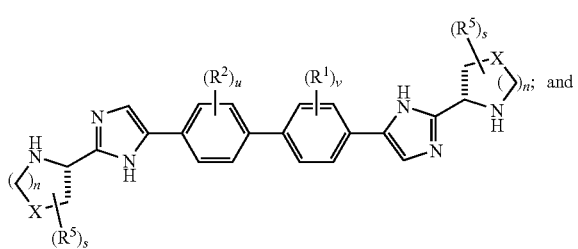

(d) treating the compound of formula (7) with a compound of formula (8)

wherein $R^9$ is as defined above.

13. The process of claim 12 wherein
  n is 1;
  s is 0;
  u and v are each 0; and
  X is $CH_2$.

14. The process of claim 12 wherein LG is a halide.

15. The process of claim 14 wherein the halide is a bromide.

16. The process of claim 12 wherein step (a) is conducted with a base.

17. The process of claim 16 wherein the base is diisopropylethylamine.

18. The process of claim 12 wherein the reagent used in step (b) is ammonium acetate.

19. The process of claim 12 wherein PG is represented by the formula:

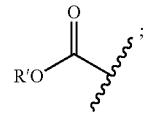

wherein
  $\mathcal{S}$ denotes the point of attachment to the parent molecular moiety; and
  R' is selected from alkyl, aryl, and arylalkyl.

20. The process of claim 19 wherein PG is tert-butoxycarbonyl.

21. The process of claim 20 wherein the deprotecting agent of step (c) is an acid.

22. The process of claim 21 wherein the acid is hydrochloric acid.

* * * * *

UNITED STATES PATENT AND TRADEMARK OFFICE
CERTIFICATE OF CORRECTION

PATENT NO. : 7,728,027 B2
APPLICATION NO. : 12/174860
DATED : June 1, 2010
INVENTOR(S) : Shawn K. Pack et al.

It is certified that error appears in the above-identified patent and that said Letters Patent is hereby corrected as shown below:

Column 16, line 20, change "6M aqueous HCl" to -- concentrated HCl --.

Claim 1:
Column 20, Line 64, after "thereof", insert -- ; --.

Claim 12:
Column 23, line 29, after "ammonia;", delete "and;".

Signed and Sealed this
Eighth Day of November, 2011

David J. Kappos
*Director of the United States Patent and Trademark Office*